(12) United States Patent
Chene et al.

(10) Patent No.: US 6,271,392 B1
(45) Date of Patent: Aug. 7, 2001

(54) INTERMEDIATES USEFUL FOR THE SYNTHESIS OF 1-ARYLPYRROLE PESTICIDES

(75) Inventors: Alain Chene, Lyons (FR); Scot Kevin Huber, Raleigh, NC (US)

(73) Assignee: Rhone-Poulenc Inc., Research Triangle Park, NC (US)

( * ) Notice: Subject to any disclaimer, the term of this patent is extended or adjusted under 35 U.S.C. 154(b) by 1241 days.

(21) Appl. No.: 08/501,336

(22) Filed: Jul. 12, 1995

Related U.S. Application Data

(63) Continuation-in-part of application No. 08/320,072, filed on Oct. 7, 1994, now abandoned.

(51) Int. Cl.[7] .................. C07D 207/36; C07D 403/12
(52) U.S. Cl. .................. 548/519; 548/541; 548/544
(58) Field of Search .................. 548/541, 544, 548/519

(56) References Cited

U.S. PATENT DOCUMENTS

| | | | |
|---|---|---|---|
| 4,112,112 | 9/1978 | Rooney et al. | 424/274 |
| 5,010,098 | 4/1991 | Brown et al. | 514/426 |
| 5,041,556 | 8/1991 | Lowen | 548/560 |
| 5,101,042 | 3/1992 | Lowen | 548/531 |
| 5,116,998 | 5/1992 | Lowen | 548/560 |
| 5,187,185 | 2/1993 | Outcalt et al. | 514/408 |
| 5,254,559 | 10/1993 | Kuhn et al. | 514/274 |
| 5,284,863 | 2/1994 | Barnes et al. | 514/427 |
| 5,302,383 | 4/1994 | Kuhn et al. | 424/84 |
| 5,359,090 | * 10/1994 | Doehner et al. | 548/561 |

FOREIGN PATENT DOCUMENTS

| | | |
|---|---|---|
| 2629877 | 1/1977 | (DE) . |
| 0460940 | 12/1991 | (EP) . |
| 0491197 | 6/1992 | (EP) . |
| 0549866 | 7/1993 | (EP) . |
| 0557732 | 9/1993 | (EP) . |
| 0600157 | 6/1994 | (EP) . |
| 50-105832 | 8/1975 | (JP) . |

OTHER PUBLICATIONS

Database CAS Questel, CN: 57338–78–0, Jan. 1976.
Database CAS Questel, CN: 27933–90–0, Jul. 1970.
Harris, *Chemical Abstracts*, vol. 73, No. 3, abstract No. 14605v (1970).
Harris, *Aust. J. Chem.*, vol. 23, No. 6, pp. 1199–1207 (1970).
Konotsune et al. CA 84:13513d, Month not available 1976.*
Foley, *Tetrahedron Letters*, vol. 35, No. 33, 5989–5992 Month not Available (1994).
Abdalla et al, *J. Heterocyclic Chem.*, 24, 297–301 Mar.–Apr. (1987).
Johnson et al, *J. Heterocyclic Chem.*, 14, 383–385 May (1977).
Derwent WPI Acc. No. 77–42179Y/24 (abstract of JP50105832, published Aug. 20, 1975).
Berlin et al, *J. Chem. Soc. Perkin Trans.*, 2, 699–704 Month not Available (1990).
Cibura et al, *J. Heterocyclic Chem.* 22, 1689–1691 Nov.–Dec. (1985).
Haas et al, *Z. anorg. allg. Chem.*, 524, 33–39 Month not Available (1985).
Haas et al, *Chem. Ber.*, 118, 4588–4596 Feb. (1985).
Harris et al, *Aust. J. Chem.*, 37, 2479–2487 Month not Available (1984).
Derwent WPI Acc. No. 80–37530C/21 (abstract of JP55051065, published Apr. 14, 1980).
Dorn et al, *Helv. Chim. Acta*, vol. 62, No. 5, 1442–1450 Month not Available (1979).
Derwent WPI Acc. No. 79–37967B/20 (abstract of JP54044669, published Apr. 9, 1979).
Derwent WPI Acc. No. 79–37966B/20 (abstract of JP54044668, published Apr. 9, 1979).
Haas et al, *Chem. Ber.* 110, 67–77 Month not Available (1977).

* cited by examiner

Primary Examiner—Laura L. Stockton
(74) Attorney, Agent, or Firm—Burns, Doane, Swecker & Mathis, L.L.P.

(57) ABSTRACT

The present invention pertains to novel 3-substituted-4-thiopyrrole intermediates for the preparation of 1-arylpyrrole compounds that are useful for the control of insects, acarids and nematodes.

The compounds, including their isomers, e.g., diastereomers and optical isomers, are compounds of a general formula (I)

(I)

R—(O)$_n$S, W, R$_1$, R$_2$, N, H (pyrrole structure)

wherein the structural variables are as defined in the description.

16 Claims, No Drawings

INTERMEDIATES USEFUL FOR THE SYNTHESIS OF 1-ARYLPYRROLE PESTICIDES

CROSS REFERENCE TO RELATED APPLICATIONS

This application is a continuation-in-part of U.S. application Ser. No. 08/320,072 filed on Oct. 7, 1994, now abandoned, which is incorporated by reference herein in its entirety and relied upon.

BACKGROUND OF THE INVENTION

1. Field of the Invention

The invention relates to new 3-substituted-4-thiopyrroles and to processes for their preparation. The invention also pertains to the application of said compounds to the preparation of pesticides for the use in agriculture for the control of arthropods, especially insects, arachnids, and nematodes.

2. Description of the Related Art

Various substituted pyrrole compounds are known to exhibit a number of different types of activity, including pharmaceutical activity and pesticidal activity. Included among these are the following:

EP 600,157 discloses a method for the chlorination of substituted pyrrole compounds.

Foley, *Tetrahedron Lett.*, 1994, 33 (5989–92), is a chemistry article which discloses 3-cyano- or 3-carboethoxypyrroles, which are substituted in the 2-position with either chlorine or alkoxy and in the 5-position with either alkyl or phenyl. There appears to be no disclosed pesticidal activity.

U.S. Pat. No. 5,302,383 and U.S. Pat. No. 5,254,559 disclose 1-(substituted)thioalkylpyrrole compounds for control of insect, acarid, and mollusk pests.

U.S. Pat. No. 5,284,863 discloses 2- or 3-phenylpyrrole compounds for control of phytopathogenic fungi.

EP 557,732 discloses 3-cyano- or 3-nitropyrrole compounds for control of helminth, acarid, and arthropod parasites of warm-blooded animals.

U.S. Pat. No. 5,187,185 discloses 1-arylpyrroles useful as insecticides.

U.S. Pat. No. 5,116,998; U.S. Pat. No. 5,101,042 and U.S. Pat. No. 5,041,556 disclose a process for the preparation of nematicidal, insecticidal, and acaricidal 2-halo-3-substituted pyrrole compounds.

U.S. Pat. No. 5,010,098 discloses 2- or 3-phenylpyrrole compounds for control of insects, acarids, and nematodes.

Abdalla et al., *J. Heterocyclic Chem.*, 1987, 24, 297–301, and Johnson et al., *J. Heterocyclic Chem.*, 1977, 14, 383–5, are chemistry articles which disclose the preparation of 2-amino-3-cyanopyrrole compounds. There appears to be no pesticidal activity.

JP 50105832 discloses substituted pyrrole compounds for use as herbicides.

EP 491,197 discloses the use of 2,3-dicyanopyrroles for the preparation of pyrrole [1,2,-b] [1,2,4]triazole cyan couplers for use in photographic film.

EP 549,866 discloses 2- or 3-phenylpyrrole compounds as insecticides and acaricides.

Berlin et al., *J. Chem. Soc. Perkin Trans.* 2, 1990, 699–704, is a chemistry article which discloses 3-thiopyrroles. There appears to be no disclosed pesticidal activity.

Cibura et al., *J. Heterocyclic Chem.*, 1985, 22, 1689–91, is a chemistry article which discloses 2- and 3-(trifluoromethylthio)pyrroles. There appears to be no disclosed pesticidal activity.

Haas et al., *Z. Anorg. Allg. Chem.*, 1985, 524, 33–9, and Haas et al., *Chem. Ber.*, 1985, 118, 4588–96, are chemistry articles which disclose tetrakis[trifluoromethyl(thio)]pyrrole compounds. There appears to be no disclosed pesficidal activity.

Harris et al., *Aust. J. Chem.*, 1984, 37, 2479–87, is a chemistry article which discloses 3-thiopyrrole compounds. There appears to be no disclosed pesticidal activity.

JP 55051065 discloses 2-amino-3,4,5-tri(tert-butylthio)pyrrole and its acetamido derivative.

Dorn et al., *Helv. Chim. Acta*, 1979, 62, 1442–50, is a chemistry article which discloses fungicidal, herbicidal, and insecticidal activity of 2,4-di(perhalomethylthio)pyrrole compounds.

JP 54044669 and JP 54044668 disclose 2,3-di(tert-butylthio)pyrrole compounds.

U.S. Pat. No. 4,112,112 and DE 2629877 disclose 3-thiopyrrole compounds as intermediates to the preparation of pyrrole[2,1-b][3]-benzapines for use as muscle relaxants or tranquilizers.

Haas et al., *Chem. Ber.*, 1977, 110, 67–77, is a chemistry article which discloses 2-, 3-, 4-, and 5-(haloalkylthio)-and-(haloformylthio)pyrroles.

It is thus apparent that the nature and position of substituent groups on substituted pyrroles provide widely different types of biological activity, which type and level of activity is not readily apparent.

SUMMARY OF THE INVENTION

The present invention pertains to novel 3-substituted-4-thiopyrrole intermediates for the preparation of 1-arylpyrrole compounds that are useful for the control of insects, acarids and nematodes.

The compounds, including their isomers, e.g., diastereomers and optical isomers, are compounds of a general formula (I)

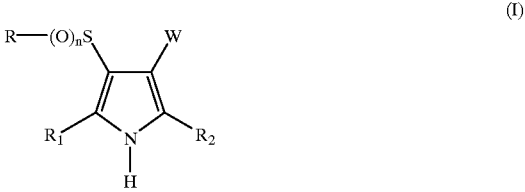

(I)

wherein:

W is cyano, $-CO_2H$, $-CO_2R_3$, $-CONH_2$, $-CONHR_3$, $-CON(R_3)_2$, $-CSNH_2$, $-CSNHR_3$, $-CSN(R3)2$, $-COSH$, $-COSR_3$, $-CHO$, $-CH=NOH$, $-CH=NOR_3$, or nitro;

R is alkyl, haloalkyl, cyano, $-C(NH_2)(=NH)$ or an acid addition salt thereof, hydrogen, or

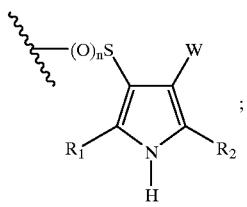

R₁ and R₂ independently represent hydrogen, halogen, alkyl, aryl, heteroaryl, haloalkyl, alkoxy, haloalkoxy, alkylsulfenyl, alkylsulfinyl, alkylsulfonyl, haloalkylsulfenyl, haloalkylsulfinyl, haloalkylsulfonyl, cyano, nitro, $NR_{11}R_{12}$, formyl, alkylcarbonyl, haloalkylcarbonyl, hydroxyalkylcarbonyl, —$CO_2H$, —$CO_2R_3$, alkylthiocarbonyl, —$CONH_2$, —$CONHR_3$, —$CON(R_3)_2$, bis(alkoxy)methyl, bis(alkylthio)methyl, (alkoxy)(cyano)methyl, (acyloxy)(cyano)methyl, (phenoxy)(cyano)methyl, (alkoxy)(alkylthio)methyl, (alkylamino)(alkoxy)methyl, (alkoxy)(dialkylamino) methyl, (alkylamino)(alkylamino)methyl, (dialkylamino)(dialkylamino)methyl, (alkoxy) (alkoxycarbonyl)methyl, (alkoxy)(aminocarbonyl) methyl, (alkoxy)(alkylaminocarbonyl)methyl, (alkoxy) (dialkylaminocarbonyl)methyl, alkoxyalkyl, hydroxyalkyl, (haloalkoxy)alkyl, (alkoxy)(haloalkyl) alkyl, cyanoalkyl, halogenated cyanoalkyl, alkoxycarbonylalkyl, aminocarbonylalkyl, monoalkylaminocarbonylalkyl, formylalkyl, dialkylaminocarbonylalkyl, alkoxyalkylcarbonyl, alkylsulfenylalkylcarbonyl, alkylsulfinylalkylcarbonyl, alkylsulfonylalkylcarbonyl, cyanoalkylcarbonyl, alkoxycarbonylalkylcarbonyl, aminocarbonylalkylcarbonyl, monalkylaminocarbonylalkylcarbonyl, dialkylaminocarbonylalkylcarbonyl, —CH=N—O—$R_{11}$, amino(thio)carbonyl, monoalkylamino(thio) carbonyl, dialylamino(thio)carbonyl, or a radical of the formula

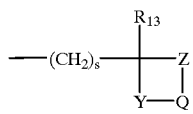

wherein:

$R_{13}$ is hydrogen, alkyl, or haloalkyl;

Y and Z are O, S, SO, $SO_2$, NH, N-alkyl, or N-acyl;

Q is ethylene or propylene optionally substituted with alkyl, haloalkyl, alkoxy, alkoxyalkyl, cyano, hydroxyalkyl, amino, alkylamino, dialkylamino, alkylsulfenyl, alkylsulfinyl, alkylsulfonyl, OH or SH;

s is 0 to 3;

$R_3$ is alkyl, haloalkyl, hydroxyalkyl or alkoxyalkyl;

$R_{11}$ and $R_{12}$ independently represent H, alkyl, haloalkyl, formyl, alkylcarbonyl, haloalkylcarbonyl, alkoxycarbonyl, haloalkoxycarbonyl, aminocarbonyl, monoalkylaminocarbonyl, dialkylaminocarbonyl, alkylsulfonyl, haloalkylsulfonyl, alkylsulfinyl, haloalkylsulfinyl, allyl, propargyl, halogen, alkoxyalkyl, alkylthioalkyl, alkylsulfinylalkyl, alkylsulfonylalkyl, haloalkoxyalkyl, haloalkylthioalkyl, haloalkylsulfmylalkyl, haloalkylsulfonylalkyl, aminoalkyl, monoalkylaminoalkyl, dialkylaminoalkyl, or alkoxycarbonyl; and n is 0, 1 or 2.

DESCRIPTION OF THE PREFERRED EMBODIMENTS

In the description, the term "alkyl" generally refers to straight- or branched-chain alkyl or cycloalkyl having up to six carbon atoms.

The term "haloalkyl" generally refers to straight- or branched-chain alkyl or cycloalkyl having up to six carbon atoms, bearing one or more halogen which are the same or different.

The term "alkoxy" generally refers to straight- or branched-chain alkoxy having up to six carbon atoms.

The term "haloalkoxy" generally refers to straight- or branched-chain alkoxy having up to six carbon atoms, bearing one or more halogen which are the same or different.

Preferred compounds of formula (I) above are those wherein W is selected from the group consisting of cyano, nitro, —CH=NOH and —CH=$NOR_3$, with cyano being most preferred.

A further preferred class of compounds of formula (I) above is that wherein R is selected from the group consisting of alkyl, haloalkyl, cyano, —$C(NH_2)(=NH)$ or an acid addition salt thereof, and

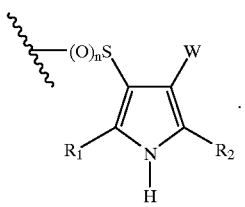

More preferably, R is selected from the group consisting of haloalkyl, cyano, —$C(NH_2)(=NH)$ or an acid addition salt thereof, and

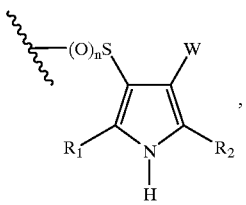

with haloalkyl being especially preferred. When R is haloalkyl, preferably it is methyl having three halogen, such as —$CF_3$ or, most preferably, —$CCl_2F$.

A further preferred class of compounds of formula (I) above is that wherein $R_1$ is selected from the group consisting of hydrogen, alkyl, haloalkyl, alkyl-$S(O)_m$ and haloalkyl-$S(O)_m$. Compounds of formula (I) above in which $R_1$ is alkyl are particularly preferred, with methyl most preferred.

Compounds of formula (I) above in which $R_2$ is selected from the group consisting of halogen, alkyl and cyano are also preferred, with halogen being particularly preferred (most preferably chlorine).

Among these compounds of formula (I) are the following preferred compounds:

1 2-chloro-3-cyano-4-thiocyanato-5-methylpyrrole;

2 4-(2-chloro-3-cyano-5-methylpyrrole)disulfide;

3 2-chloro-3-cyano-4-(dichlorofluoromethyl)sulfenyl-5-methylpyrrole;

4 2-methoxy-3-cyano-4-(dichlorofluoromethyl)sulfenyl-5-methylpyrrole;

5 2-chloro-3-cyano-5-methyl-4-thiouroniumpyrrole hydrobromide;

6 2-chloro-3-cyano-4-(dichlorofluoromethyl)sulfonyl-5-methylpyrrole;

7 2-chloro-3-cyano-4thiocyanato-5-cyclopropylpyrrole;

8 4-(2-chloro-3-cyano-5-cyclopropylpyrrole)disulfide;

9 2-chloro-3-cyano-4-(dichlorofluoromethylsulfenyl)-5-cyclopropylpyrrole;

10 2-chloro-3-cyano-4-thiocyanato-5-phenylpyrrole;

11 2-chloro-3-cyano-4-thiocyanato-5-isopropylpyrrole;

12 4-(2-chloro-3-cyano-5-isopropylpyrrole)disulfide;

13 2-chloro-3-cyano-4-(dichlorofluoromethylsulfenyl)-5-isopropylpyrrole; and 14 2-chloro-3-cyano-4-(bromodifluoromethylsulfenyl)-5-methylpyrrole.

It is an object of the present invention to provide new intermediates to pesticidal compounds of the 1-arylpyrrole family together with processes for their preparation.

The second object of the present invention is to provide compounds with a rather simple chemical formula that are readily prepared from known and/or readily available and frequently inexpensive intermediates and starting materials.

The compounds of general formula (I) can be prepared by the application or adaptation of known methods (i.e., methods heretofore used or described in the chemical literature), for example as described hereinbelow.

According to a further feature of the present invention, compounds of general formula (I) in which R is alkyl, haloalkyl, cyano, —C(NH$_2$)(=NH) or disulfide and n is zero, can be prepared by the reaction of an intermediate pyrrole of formula (II):

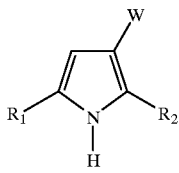

(II)

wherein R$_1$, R$_2$ and W are as defined above, with:

1) an alkyl or haloalkylthiohalide to give compounds wherein R is alkyl or haloalkyl; or 2) an activated disulfur compound such as S$_2$Cl$_2$, (SCN)$_2$, or SC(NH$_2$)$_2$/Br$_2$ to give a compound wherein R is cyano, —C(NH$_2$)(=NH), or disulfide; which may be optionally reacted with an alkylating or haloalkylating agent, in the presence of a reducing medium such as NaBH$_4$, SO$_2$/NaO$_2$CH, or Na$_2$S$_2$O$_3$ to give compounds wherein R is alkyl or haloalkyl.

The proper conditions for sulfenylation will depend upon the nature of the starting materials and the product formed, that is to say solubility, reactivity, stability, etc. In general, reaction will be performed optionally in a suitable solvent, at a temperature between −100 and 100° C. While such conditions may be required to be individually selected, in general, the compounds of formula (I) can readily be prepared by known sulfenylation methods such as those described in Clavel et al., J. Chem. Soc. Perkin Trans 1, 1992, 3371–5; Grant et al., J. Am. Chem. Soc., 1960, 82, 2742–4; Haas et al., Chemiscbe Ber., 1977, 110, 67–77; and U.S. Pat. No. 5,197,185.

According to a further feature of the present invention compounds of formula (I) in which n is one or two may be prepared by oxidizing the corresponding compounds of formula (I) in which n is zero or one. The reaction is performed by known methods, e.g., treatment with 3-chloroperbenzoic acid or hydrogen peroxide, optionally in a solvent and optionally in the presence of a catalyst.

Compounds of formula (II) above are known or can be prepared by methods or processes, for example as described in Foley, Tetrahedron Lett., 1994, 33 (5989–92); EP 557, 732, published Sep. 1, 1993; U.S. Pat. No. 5,116,998, issued May 26, 1992; U.S. Pat. No. 5,101,042, issued Mar. 31, 1992; U.S. Pat. No. 5,041,556, issued Aug. 20, 1991; and Davies et al., J. Chem. Soc., 1994 (126–131); all of which are incorporated herein by reference.

Compounds of formula (II) in which R$_1$ is Cl, Br, I, F, cyano, or nitro may be prepared by treatment of the corresponding compound of formula (II) in which R$_1$ is hydrogen with a suitable electrophilic reagent (e.g., N-chlorosuccinimide, bromine, iodine, xenon difluoride, chlorosulfonylisocyanate or nitric acid) by well-known methods, as described, for example, by Jackson et al. in Heterocyclic Compounds, Vol. 48, Part 1, John Wiley and Sons, New York, 1990, Chapter 3.

Compounds of formula (II) above in which R$_1$ is hydrogen, alkyl, haloalkyl, alkylcarbonyl, haloalkylcarbonyl, aryl, heteroaryl, alkoxycarbonyl, haloalkoxycarbonyl, —CONH$_2$, —CONHR$_3$, —CON(R$_3$)$_2$, alkylthiocarbonyl, amino(thio)carbonyl, monoalkylamino(thio)carbonyl, or dialkylamino(thio)carbonyl and R$_2$ is Cl, Br, F, I, alkoxy, haloalkoxy, alkylthio, haloalkylthio, cyano, or amino may also be prepared by treatment of a compound of formula (III)

R$_6$C(=O)—CH$_2$CH(W)—CN    (III)

wherein R$_6$ is hydrogen, alkyl, haloalkyl, alkylcarbonyl, haloalkylcarbonyl, aryl, heteroaryl, alkoxycarbonyl, haloalkoxycarbonyl, —CONH$_2$, —CONHR$_3$, —CON(R$_3$)$_2$, alkylthiocarbonyl, amino(thio)carbonyl, monoalkylamino(thio)carbonyl, or dialkylamino(thio)carbonyl, with a nucleophilic compound HB wherein B is Cl, Br, F, I, alkoxy, haloalkoxy, alkylthio, haloalkylthio, cyano, or amino (optionally in a suitable solvent at a temperature of 0–100° C.) and optionally in the presence of a catalyst (e.g., formic acid or dimethylammonium chloride) to give pyrrole compounds of general formula (II) wherein R$_{11}$=R$_6$ and R$_2$ is as defined earlier in this paragraph.

Compounds of formula (II) in which R$_1$ or R$_2$ is —NR$_{11}$R$_{12}$ wherein R$_{11}$ and/or R$_{12}$ are not H, are prepared by alkylation, or other well-known methods of chemistry, of compounds of formula (II) wherein R$_1$ or R$_2$=NR$_{11}$R$_{12}$ where R$_{11}$ and/or R$_{12}$=H, such as those described in Greene et al., Protective Groups in Organic Chemistry; John Wiley and Sons, Inc.; New York; 1991; Chapter 7.

Compounds of formula (II) in which R$_1$ or R$_2$ is alkenyl, haloalkenyl, aryl, heteroaryl, cyanoalkenyl, or alkoxycarbonylalkenyl, are prepared from the corresponding compound of formula (I) in which R$_1$ or R$_2$ is NH$_2$ by treatment with a diazotizing reagent (e.g., tert-butylnitrite, sodium nitrite, nitrous acid, or a similar reagent) to form an intermediate diazonium salt of formula (II) (in which R$_1$ or R$_2$ is replaced by N$_2^+$), followed by treatment with an alkene, haloalkene, arene, heteroarene, cyanoalkene, or carbonylalkene compound, optionally in a suitable solvent and optionally in the presence of a copper salt. This chemistry is well-known and described by Rondestvedt, Jr. in *Organic Reactions*, Vol. 24; John Wiley and Sons, Inc., New York; 1976; Chapter 3. Alternatively, compounds of formula (II) in which $R_1$ and $R_2$ are as defined at the beginning of this paragraph can be prepared by a palladium catalyzed coupling of an organotin compound of formula (alkyl)$_3$SnR$_7$ (wherein $R_7$ is alkenyl or aryl) with a compound of formula (II) wherein $R_1$ and/or $R_2$=halo, according to the method of or by a modification of the method of Bailey, *Tetrahedron Lett.*; 1986, 27, 4407–4410, to give compounds of formula (II) wherein $R_1$ and/or $R_2$=$R_7$.

Compounds of formula (II) in which $R_1$ or $R_2$ is —CHO are prepared by a number of well-known methods from the corresponding compounds of formula (II) in which $R_1$ or $R_2$ is alkenyl, as described, for example, in Larock, *Comprehensive Organic Transformations*, VCH Publishers, Inc., New York, 1989, pages 593–596.

Compounds of formula (II) in which $R_1$ or $R_2$ is alkylcarbonyl, haloalkylcarbonyl, hydroxyalkylcarbonyl, —CO$_2$H, —CO$_2$R$_3$, alkylthiocarbonyl, —CONH$_2$, —CONHR$_3$, —CON(R$_3$)$_2$, bis(alkoxy)methyl, bis(alkylthio)methyl, (alkoxy)(cyano)methyl, (acyloxy)(cyano)methyl, (phenoxy)(cyano)methyl, (alkoxy)(alkylthio)methyl, (alkylamino)(alkoxy)methyl, (alkoxy)(dialkylamino)methyl, (alkylamino)(alkylamino)methyl, (dialkylamino)(dialkylamino)methyl, (alkoxy)(alkoxycarbonyl)methyl, (alkoxy)(aminocarbonyl)methyl, (alkoxy)(alkylaminocarbonyl)methyl, (alkoxy)(dialkylaminocarbonyl)methyl, alkoxyalkyl, hydroxyalkyl, (haloalkoxy)alkyl, (alkoxy)(haloalkyl)alkyl, cyanoalkyl, halogenated cyanoalkyl, alkoxycarbonylalkyl, aminocarbonylalkyl, monoalkylaminocarbonylalkyl, formylalkyl, dialkylaminocarbonylalkyl, alkoxyalkylcarbonyl, alkyl-S(O)$_m$alkylcarbonyl, cyanoalkylcarbonyl, alkoxycarbonylalkylcarbonyl, aminocarbonylalkylcarbonyl, monalkylaminocarbonylalkylcarbonyl, dialkylaminocarbonylalkylcarbonyl, CH=N—O—R$_{11}$, amino(thio)carbonyl, monoalkylamino(thio)carbonyl, dialkylamino(thio)carbonyl, or

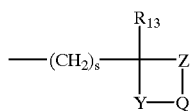

can be readily prepared from compounds of formula (II) in which $R_1$ or $R_2$ is —CHO by numerous well-known methods of organic chemistry, such as those described in Larock, pages 838–840, 689–692, 966–976, and 562, and in Greene et al., pages 217–210.

Compounds of formula (III) above may be prepared by reacting a cyano compound of formula (IV):

wherein W is as defined above, with a carbonyl compound of general formula (V)

wherein $R_6$ is as defined above and L is a leaving group, e.g., halogen, sulfonate ester or hydroxy. The reaction is generally carried out according to the method of Sainsbury et al., *Tetrahedron Lett.*, 1988, 29, 6505–8, or Toja et al., *Synthesis*, 1986, 272.

Compounds of formula (II) wherein $R_1$ or $R_2$ is alkylsulfenyl, haloalkylsulfenyl, alkylthioalkyl, haloalkylthioalkyl, or alkylsulfenylalkylcarbonyl may be oxidized to compounds of formula (II) in which $R_1$ or $R_2$ is alkylsulfinyl, alkylsulfonyl, haloalkylsulfinyl, haloalkylsulfonyl, alkylsulfinylalkyl, alkylsulfonylalkyl, haloalkylsulfinylalkyl, haloalkylsulfonylalkyl, alkylsulfinylalkylcarbonyl, or alkylsulfonylalkylcarbonyl. The reaction is performed by known methods, e.g., treatment with 3-chloroperbenzoic acid or hydrogen peroxide, optionally in a solvent and optionally in the presence of a catalyst.

Compounds of formulas (I) and (V) above are known or can be prepared using known methods.

Thiopyrrole compounds of general formula (I) are useful for the preparation of 1-arylpyrrole compounds of general formula (VII), which are useful as pesticides as described in U.S. Pat. No. 5,187,185, and copending U.S. patent application Ser. No. 08/320,071 filed on Oct. 7, 1994. Pesticidally active compounds of general formula (VII) may be prepared from compounds of general formula (I) by e.g., treatment of a compound of general formula (I) with an arylating agent (VI), preferably in the presence of a base (e.g., sodium hydride, sodium hydroxide, or potassium carbonate) in a suitable solvent, and at a temperature between 0–15° C., according to the scheme:

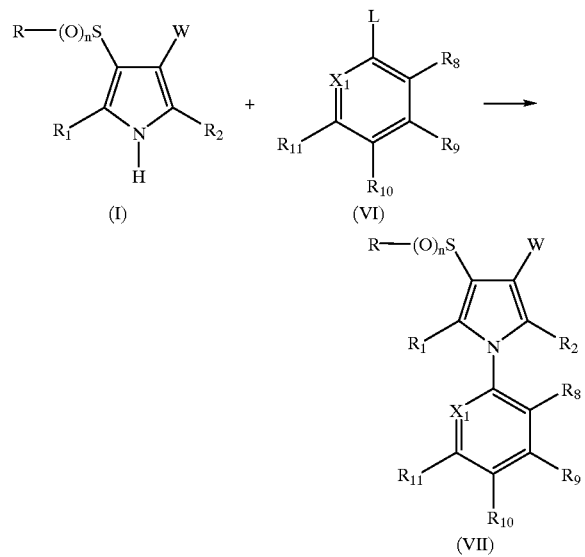

Compounds of general formula (VI) are aromatic compounds in which L is a leaving group and $X_1$ and $R_8$–$R_{11}$, are chosen to give insecticidally active compounds (VII), for example as described in U.S. Pat. No. 5,187,185 and copending U.S. patent application Ser. No. 08/320,071 filed on Oct. 7, 1994, both of which are incorporated by reference herein in their entireties and relied upon. The aromatic compounds of formula (VI) are generally known compounds of organic chemistry and usually commercially available or can be prepared from such available compounds by known methods. Several compounds of formula (VI) have been used in a similar manner as intermediates for the synthesis of a number of pesticidal heterocyclic compounds such as phenylpyridones in EP 367,410, 1-(2-pyridyl)pyridones in EP 272,824, phenylpyrimid-6-one derivatives in U.S. Pat. No. 5,104,878, 1-aryl-2-yl-pyrazine-2-one derivatives in EP 408,196, pyridylpyrimidinone derivatives in EP 357,201, pyrimidinone derivatives in EP 338,686 or arylindazoles in WO 93/18008.

REPRESENTATIVE COMPOUNDS OF THE INVENTION

The compounds of TABLE 1 are illustrative of some of the preferred compounds or subgroups of compounds within the purview of the above general formula (I) and can be prepared by the herein described methods or processes of synthesis, by the appropriate selection of reactants, conditions and procedures, which are commonly known and apparent to one skilled in the art.

TABLE 1

REPRESENTATIVE 3-SUBSTITUTED-4-THIOPYRROLES

| W | R | n | $R_1$ | $R_2$ |
|---|---|---|-------|-------|
| CN | Me | 0 | H | $OCF_3$ |
| $CO_2Me$ | $CF_3$ | 0 | Me | OMe |
| $CO_2CH_2CF_3$ | $CClF_2$ | 1 | $CHMe_2$ | $OCF_3$ |
| $CO_2CH_2CH_2OH$ | $CCl_2F$ | 1 | $CF_3$ | $NH_2$ |
| $CO_2H$ | CN | 1 | CN | NHAc |
| $CONH_2$ | $C(NH_2)(=NH)$—HBr | 0 | $OCF_3$ | NHMe |
| CONHMe | $CF_3$ | 2 | OMe | $NMe_2$ |
| $CONMe_2$ | Me | 2 | $OCF_3$ | Cl |
| $CON(CH_2CH_2OH)_2$ | $CCl_2F$ | 1 | $NH_2$ | $SCF_3$ |
| CN | $CCl_2F$ | 1 | OMe | Me |
| COSMe | $CF_3$ | 2 | NHAc | $SCH_3$ |
| $COSCF_3$ | Me | 0 | NHMe | $SOCF_3$ |
| CHO | $C(NH_2)(=NH)$—HBr | 2 | $NMe_2$ | $SOCH_3$ |
| $CSNH_2$ | $CClF_2$ | 1 | Cl | $SO_2CH_3$ |
| CSNHMe | CN | 1 | Br | $SO_2CF_3$ |
| $CSNMe_2$ | $CF_3$ | 0 | F | $COCH_3$ |
| $NO_2$ | Me | 2 | CN | $CH(NMe_2)OMe$ |
| CN | $CCl_2F$ | 1 | OMe | Cl |
| $CON(CH_2CH_2OH)_2$ | $CF_3$ | 0 | CHO | $CH(SMe)OMe$ |
| COSMe | $CClF_2$ | 0 | $CO_2Me$ | $CH(OMe)CO_2CH_3$ |
| $COSCF_3$ | $CCl_2F$ | 1 | $CO_2CH_2CH_2OH$ | $CH(OMe)CONH_2$ |
| CHO | CN | 1 | $CO_2H$ | $CH(OMe)CONMe_2$ |
| $CSNH_2$ | $C(NH_2)(=NH)$—HBr | 1 | $CO_2CH_2CH_2Cl$ | $CH(OMe)_2$ |
| CSNHMe | $CF_3$ | 0 | $CONH_2$ | $COCF_3$ |
| $CSNMe_2$ | Me | 2 | CONHMe | $COCH_2OH$ |
| $NO_2$ | $CCl_2F$ | 2 | $CONMe_2$ | $CH_2OCH_3$ |
| CN | $CF_3$ | 1 | $CON(CF_3)_2$ | $CH_2OH$ |
| $CO_2Me$ | Me | 2 | $CONHCH_2CH_2OH$ | $CH_2OCF_3$ |
| $CO_2CH_2CF_3$ | $C(NH_2)(=NH)$—HBr | 0 | $SCF_3$ | CHCNOMe |
| $CO_2CH_2CH_2OH$ | $CClF_2$ | 2 | $SCH_3$ | $CH(Me)OMe$ |
| $CO_2H$ | CN | 1 | $SOCF_3$ | $CH(CF_3)OMe$ |
| $CONH_2$ | $CF_3$ | 1 | $SOCH_3$ | H |
| CN | $CCl_2F$ | 2 | Cl | $NH_2$ |
| CONHMe | Me | 0 | $SO_2CH_3$ | Me |
| $CONMe_2$ | Me | 2 | $SO_2CF_3$ | $CHMe_2$ |
| CN | $CF_3$ | 2 | $COCH_3$ | $CF_3$ |
| $CO_2Me$ | $CClF_2$ | 0 | $COCF_3$ | CN |
| $CO_2CH_2CF_3$ | $CCl_2F$ | 0 | $COCH_2OH$ | Br |
| $CO_2CH_2CH_2OH$ | CN | 1 | $CH_2OCH_3$ | F |
| $CO_2H$ | $C(NH_2)(=NH)$—HBr | 1 | $CH_2OH$ | CN |
| $CONH_2$ | $CF_3$ | 1 | $CH_2OCF_3$ | CHO |
| CN | $CCl_2F$ | 2 | NHMe | CN |
| CONHMe | Me | 0 | CHCNOMe | $CO_2Me$ |
| $CONMe_2$ | $CCl_2F$ | 2 | $CH(Me)OMe$ | $CO_2CH_2CH_2OH$ |
| CN | $CF_3$ | 2 | $CH(CF_3)OMe$ | $CO_2H$ |
| $CO_2Me$ | Me | 1 | $CH(NMe_2)OMe$ | $CO_2CH_2CH_2Cl$ |
| $CO_2CH_2CF_3$ | $C(NH_2)(=NH)$—HBr | 2 | $CH(SMe)OMe$ | $CONH_2$ |
| $CO_2CH_2CH_2OH$ | $CClF_2$ | 0 | $CH(OMe)CO_2CH_3$ | CONHMe |
| $CO_2H$ | CN | 2 | $CH(OMe)CONH_2$ | $CONMe_2$ |
| $CONH_2$ | $CF_3$ | 1 | $CH(OMe)CONMe_2$ | $CON(CF_3)_2$ |
| CONHMe | Me | 1 | $CH(OMe)_2$ | $CONHCH_2CH_2OH$ |

DETAILED EXAMPLES OF COMPOUND SYNTHESIS

The following EXAMPLES 1 to 7 and 10 to 18 illustrate detailed methods of synthesis and the physical properties of representative compounds of formula (I) (and their chemical intermediates) according to the invention. EXAMPLES 8 and 9 illustrate use of the compounds of formula (I) as intermediates in the synthesis of 1-arylpyrrole pesticides. Reported melting points for the compounds in these EXAMPLES represent the high value of an observed melting point range determined for a compound. Additionally, one or more spectroscopic analyses (IR, $^1H$ or $^{19}F$ NMR, MS, etc.) have been performed on each compound for characterization and confirmation of the chemical structure.

Suitable diluents, which in some cases may be optional, for carrying out the process are inert, organic solvents, which include aliphatic, alicyclic or aromatic, or optionally halogenated hydrocarbons, for example, benzene, chlorobenzene, toluene or xylene.

EXAMPLE 1

2-Chloro-3-cyano-5-methylpyrrole

Hydrogen chloride was bubbled through a solution of 2-cyano-4-oxopentanenitrile (2.1 g) in 20 ml of $CH_2Cl_2$ and 20 ml of dioxane for 15 min. The mixture was stirred for 1.5 h, then poured into water and extracted with methylene chloride. The organic extracts were dried over $MgSO_4$. Silica gel chromatography allowed isolation of a white solid (3.1 g), m.p. 157° C.

EXAMPLE 2
2-Chloro-3-cyano-4-thiocyanato-5-methylpyrrole (Compound 1)

A solution of sodium thiocyanate (7.5 g) in 50 ml of methanol was cooled to −76° C. Bromine in 30 ml of cold methanol was added dropwise over 12 min. A slurry of 2-chloro-3-cyano-5-methylpyrrole in 30 ml of cold methanol was added at once. After stirring 30 min at −78° C., the mixture was poured into $H_2O$ and stirred overnight, then filtered, washed with water and hexane, and air dried to afford 6.57 g of an off-white solid, m.p. 171° C.

EXAMPLE 3
4-(2-Chloro-3-cyano-5-methylpyrrole)disulfide (Compound 2)

A solution of 2-chloro-3-cyano-4-thiocyanato-5-methylpyrrole (2.4 g) in 30 ml of methanol was cooled in an ice bath and treated with $NaBH_4$ (1.06 g), added over 40 min. After addition was completed, the mixture was heated to reflux for 40 min., then cooled to room temperature and diluted with 65 ml of water. The resulting solid was collected by filtration, washed with water and hexane, and air-dried to afford 1.01 g of tan solid, m.p. >230° C. (dec.).

EXAMPLE 4
2-Chloro-3yano-4-(dichlorofluoromethyl)sulfeny-5-methylpyrrole (Compound 3)

A solution of 4-(2-chloro-3-cyano-5-methylpyrrole) disulfide (1.6 g) in 50 ml of NMP (N-methylpyrrolidinone) in a pressure bottle was treated with sodium formate (1.92 g). Fluorotrichloromethane (17 ml) was added, the mixture was cooled to −50° C., and sulfur dioxide (8 ml) was added. The bottle was sealed under a pressure gauge and allowed to warm to room temperature. After stirring at room temperature overnight, the mixture was vented. Nitrogen was bubbled through the mixture for 2 h to remove $SO_2$. The solvent was removed under reduced pressure. The resulting brown oil was dissolved in 50 ml of EtOAc, washed with water, and dried over $MgSO_4$. Silica gel chromatography afforded 1.07 g of a pale yellow solid, m.p. 187° C.

EXAMPLE 5
2-Methoxy-3-cyano-5-methylpyrrole

A solution of 2-cyano-4-oxopentanenitrile (2.75 g) and dimethylamine hydrochloride (16.25 g) in 100 ml of methanol was heated at reflux for 24 h. The mixture was cooled to room temperature and the solvents were removed under reduced pressure. The residue was dissolved in 50 ml of $H_2O$ and extracted with EtOAc. The organic extracts were dried over $Na_2SO_4$. Silica gel chromatography afforded a white solid (0.8 g), m.p. 105° C.

EXAMPLE 6
2-Methoxy-3-cyano-4-(dichlorofluoromethyl)sulfenyl-5-methylpyrrole (Compound 4)

A suspension of 2-methoxy-3-cyano-5-methylpyrrole (0.5 g) in 5 ml of $CH_2Cl_2$ was treated with $Cl_2FCSCl$ (0.45 ml) and stirred at room temperature for 14 h. The resulting precipitate was filtered, washed with $CH_2Cl_2$, and dried under high vacuum to afford an off-white solid (0.59 g), m.p. 175° C.

EXAMPLE 7
2-Cloro-3-cyano-5-methvl-4-thiouronium-pyrrole hydrobromide (Compound 5)

A suspension of thiourea in 10 ml of acetic acid under $N_2$ was treated with bromine. After 10 min. 2-chloro-3-cyano-5-methylpyrrole was added, followed by 10 ml of AcOH. After stirring overnight, the mixture was filtered and the collected solid was washed with acetic acid and ether and air dried to afford a tan powder (1.86 g), m.p. 165° C. (dec).

EXAMPLE 8
1-(2,6-dinitro-4-trifluoromethylphenyl)-2-chloro-3-cyano-4-dichlorofluoro-methylsulfenyl-5-methylpyrrole A mixture of 2-chloro-3-cyano-4-(dichlorofluoromethylsulfenyl)-5-methyl pyrrole (1 g), 4-chloro-3,5-dinitrobenzotrifluoride (2 g, 2 eq.) and anhydrous potassium carbonate (0.56 g) in sulfolane was heated at 75° C. overnight, poured into water, and extracted with diethyl ether several times. The combined ether solution was washed with water, dried over $MgSO_4$, filtered and concentrated in vacuo. The crude material was purified via silica gel column chromatography eluted with ethyl acetate and hexane. The desired product (1.3 g) was obtained as a yellow solid, m.p. 152.5–154° C.

EXAMPLE 9
1-(2-chloro-6-nitro-4-trifluoromethylphenyl)-2-chloro-3-cyano-4-dichlorofluoromethylsulfenyl-5-methylpyrrole A mixture of 1-H-2-chloro-3-cyano-4-dichlorofluoromethylsulfenyl-5-methylpyrrole (5.47 g, 20 mmol), 3-chloro-4-fluoro-5-nitrobenzotrifluoride (7.3 g, 1.5 eq.; prepared from reaction of 3,4-dichloro-5-nitrobenzotrifluoride, potassium fluoride and tetramethylammonium chloride), potassium carbonate (3.04 g, 1.1 eq.) and sulfolane was heated at 80° C., cooled to ambient temperature when it was done, poured into water and extracted with diethyl ether. The organic layer was washed with water, dried over sodium sulfate, filtered and concentrated in vacuo. The desired product (7.26 g) was obtained after chromatography, m.p. 116–118° C.

EXAMPLE 10
2-Chloro-3-cyano-4-(dichlorofluoromethylsulfonyl)-5-methylpyrrole (Compound 6)

A mixture of 2-chloro-3-cyano-4-(dichlorofluoromethylsulfenyl)-5-methyl-pyrrole (2.74 g) and MCPBA (4.75 g) in 20 ml of 1,2-dichloroethane was heated at reflux for 2 h. The mixture was cooled to room temperature, diluted with 100 ml of ether, and washed with 50 ml of 10% $Na_2S_2O_3$, 50 ml of 10% $K_2CO_3$, and 50 ml of sat. NaCl. The combined aqueous washings were extracted with 2×50 ml of ether. The combined organic solutions were dried over $MgSO_4$, filtered, and evaporated to a yellow solid (1.8 g), m.p. 187° C. (dec.).

EXAMPLE 11
2-Chloro-3-cyano-4-thiocyanato-5-cyclopropylpyrrole

A. 2-Chloro-3-cyano-5-cyclopropylpyrrole was prepared according to the method of EXAMPLE 1 from 2-cyano-4-cyclopropyl-4-oxobutanenitrile (prepared from bromomethylcyclopropyl ketone and malononitrile by a modification of the method of Sainsbury et al.).

B. 2-Chloro-3-cyano-4-thiocyanato-5-cyclopropylpyrrole (melting point 123° C.) was prepared from 2-chloro-3-cyano-5-cyclopropylpyrrole by the method of EXAMPLE 2.

EXAMPLE 12
4-(2-Chloro-3-cyano-5-cyclopropylpyrrole)disulfide (melting point >230° C.) was prepared from 2-chloro-3-cyano-4-thiocyanato-5-cyclopropylpyrrole by the method of EXAMPLE 3.

EXAMPLE 13

2-Chloro-3-cyano-4-(dichlorofluoromethylsulfenyl)-5-cyclopropylpyrrole (melting point 120° C.) was prepared from 4(2-chloro-3-cyano-5-cyclopropylpyrrole)disulfide by the method of EXAMPLE 4.

EXAMPLE 14

2-Chloro-3-cyano-4-thiocyanato-5-phenylpyrrole

A. 2-Chloro-3-cyano-5-phenylpyrrole was prepared according to the method of EXAMPLE 1 from 2-cyano-4-phenyl-4-oxobutanenitrile (prepared from bromomethylphenyl ketone and malononitrile by a modification of the method of Sainsbury et al.).

B. 2-Chloro-3-cyano-4-thiocyanato-5-phenylpyrrole (melting point 159° C.) was prepared from 2-chloro-3-cyano-5-phenylpyrrole by the method of EXAMPLE 2.

EXAMPLE 15

2-Chloro-3-cyano-4-thiocyanato-5-isopropylpyrrole

A. 2-Chloro-3-cyano-5-isopropylpyrrole was prepared according to the method of EXAMPLE 1 from 2-cyano-5-methyl-4-oxobexanenitrile (prepared from bromomethylisopropyl ketone and malononitrile by a modification of the method of Sainsbury et al.).

B. 2-Chloro-3-cyano-4-thiocyanato-5-isopropylpyrrole (melting point 159° C.) was prepared from 2-chloro-3-cyano-5-isopropylpyrrole by the method of EXAMPLE 2.

EXAMPLE 16

4-(2-Chloro-3-cyano-5-isopropylpyrrole)disulfide [$^1$H NMR (300 MHz; DMSO-$d_6$) δ: 1.03 (d, 6H, J=7.1 Hz), 2.94 (septet, 1H, J=7.0 Hz), 12.79 (s, 1H)] was prepared from 2-chloro-3-cyano-4-thiocyanato-5-isopropylpyrrole by the method of EXAMPLE 3.

EXAMPLE 17

2-Chloro-3-cyano-4-(dichlorofluoromethylsulfenyl)-5-isopropylpyrrole (melting point 120° C.) was prepared from 4-(2-chloro-3-cyano-5-isopropylpyrrole)disulfide by the method of EXAMPLE 4.

EXAMPLE 18

2-Chloro-3-cyano-4-(bromodifluoromethylsulfenyl)-5-methylpyrrole (melting point 190° C.) was prepared from 4-(2-chloro-3-cyano-5-methylpyrrole)disulfide and dibromodifluoromethane by the method of EXAMPLE 4.

The compounds of formula (I) are useful in the preparation of 1-arylpyrrole pesticides of the formula

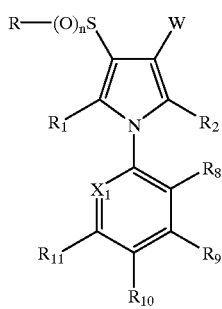

(VII)

See e.g., U.S. Pat. No. 5,187,185 and copending U.S. patent application Ser. No. 08/320,071 filed on Oct. 7, 1994.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound of the formula:

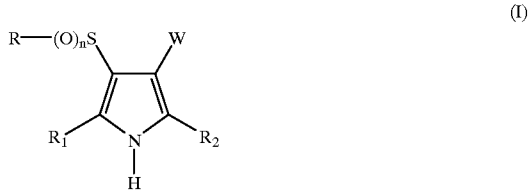

(I)

wherein:

W is cyano, —$CO_2H$, —$CO_2R_3$, —$CONH_2$, —$CONHR_3$, —$CON(R_3)_2$, —$CSNH_2$, —$CSNHR_3$, —$CSN(R_3)_2$, —$COSH$, —$COSR_3$, —$CHO$, —$CH=NOH$, —$CH=NOR_3$, or nitro;

R is alkyl, haloalkyl, cyano, —$C(NH_2)(=NH)$ or an acid addition salt thereof, hydrogen, or

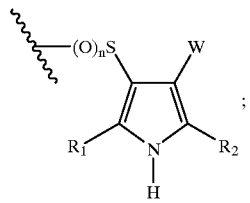

;

$R_1$ and $R_2$ independently represent hydrogen, halogen, alkyl, haloalkyl, alkoxy, haloalkoxy, alkylsulfenyl, alkylsulfinyl, alkylsulfonyl, haloalkylsulfenyl, haloalkylsulfinyl, haloalkylsulfonyl, cyano, nitro, $NR_{11}R_{12}$, formyl, alkylcarbonyl, haloalkylcarbonyl, hydroxyalkylcarbonyl, —$CO_2H$, —$CO_2R_3$, alkylthiocarbonyl, —$CONH_2$, —$CONHR_3$, —$CON(R_3)_2$, bis(alkoxy)methyl, bis(alkylthio)methyl, (alkoxy)(cyano)methyl, (acyloxy)(cyano)methyl, (phenoxy)(cyano)methyl, (alkoxy)(alkylthio)methyl, (alkylamino)(alkoxy)methyl, (alkoxy)(dialkylamino)methyl, (alkylamino)(alkylamino)methyl, (dialkylamino)(dialkylamino)methyl, (alkoxy)(alkoxycarbonyl)methyl, (alkoxy)(aminocarbonyl)methyl, (alkoxy)(alkylaiinocarbonyl)methyl, (alkoxy)(dialkylaminocarbonyl)methyl, alkoxyalkyl, hydroxyalkyl, (haloalkoxy)alkyl, (alkoxy)(haloalkyl)alkyl, cyanoalkyl, halogenated cyanoalkyl, alkoxycarbonylalkyl, aminocarbonylalkyl, monoalkylaminocarbonylalkyl, formylalkyl, dialkylaminocarbonylalkyl, alkoxyalkylcarbonyl, alkylsulfenylalkylcarbonyl, alkylsulfmylalkylcarbonyl, alkylsulfonylalkylcarbonyl, cyanoalkylcarbonyl, alkoxycarbonylalkylcarbonyl, aminocarbonylalkylcarbonyl, monalkylaminocarbonylalkylcarbonyl, dialkylaminocarbonylalkylcarbonyl, —$CH=N—O—R_{11}$, amino(thio)carbonyl, monoalkylamino(thio) carbonyl, dialkylamino(thio)carbonyl, or a radical of the formula

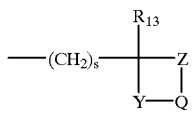

wherein:
R₁₃ is hydrogen, alkyl, or haloalkyl;
Y and Z are O, S, SO, SO₂, NH, N-alkyl, or N-acyl;
Q is ethylene or propylene optionally substituted with alkyl, haloalkyl, alkoxy, alkoxyalkyl, cyano, hydroxyalkyl, amino, alkylamino, dialkylamino, alkylsulfenyl, alkylsulfmyl, alkylsulfonyl, OH, or SH;
s is 0 to 3;
R₃ is alkyl, haloalkyl, hydroxyalkyl or alkoxyalkyl;
R₁₁, and R₁₂ independently represent H, alkyl, haloalkyl, formyl, alkylcarbonyl, haloalkylcarbonyl, alkoxycarbonyl, haloalkoxycarbonyl, aminocarbonyl, monoalkylaminocarbonyl, dialkylaminocarbonyl, alkylsulfonyl, haloalkylsulfonyl, alkylsulfinyl, haloalkylsulfimyl, allyl, propargyl, halogen, alkoxyalkyl, alkylthioalkyl, alkylsulfinylalkyl, alkylsulfonylalkyl, haloalkoxyalkyl, haloalkylthioalkyl, haloalkylsulfmylalkyl, haloalkylsulfonylalkyl, aminoalkyl, monoalkylaminoalkyl, dialkylaminoalkyl, or alkoxycarbonyl; and
n is 0, 1 or 2,
provided that when R₁ is methyl, then R₂ is not hydrogen or alkyl, W is not —CO₂R₃ and n is not 0; and
provided that when W is —CO₂C₂H₅, then R is not —C(NH₂)(=NH) or an acid addition salt thereof.

2. A compound according to claim 1 in which W is selected from the group consisting of cyano, nitro, —CH=NOH and —CH=NOR₃, wherein R₃ is as defined in claim 1.

3. A compound according to claim 2 in which W is cyano.

4. A compound according to claim 1 in which R is selected from the group consisting of haloalkyl, cyano, —C(NH₂)(=NH) or an acid addition salt thereof, and

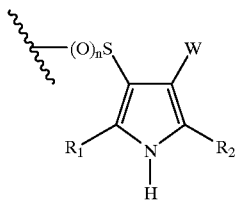

wherein W, R₁, R₂ and n are as defined in claim 1.

5. A compound according to claim 4 in which R is haloalkyl.

6. A compound according to claim 1 in which R₁ is selected from the group consisting of hydrogen, alkyl, haloalkyl, alkylsulfenyl, alkylsulfinyl, aikylsulfonyl, haloalkylsulfenyl, haloalkylsulfinyl, and haloalkylsulfonyl.

7. A compound according to claim 6 in which R₁ is alkyl.

8. A compound according to claim 7 in which R₁ is methyl.

9. A compound according to claim 1 in which R₂ is selected from the group consisting of halogen, alkyl and cyano.

10. A compound according to claim 9 in which R₂ is halogen.

11. A compound according to claim 10 in which R₂ is chlorine.

12. A compound according to claim 1 in which:
W is selected from the group consisting of cyano, nitro, —CH=NOH and —CH=NOR₃, wherein R₃ is as defined in claim 1;
R is selected from the group consisting of alkyl, haloalkyl, cyano, —C(NH₂)(=NH) or an acid addition salt thereof, and

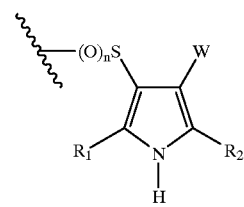

wherein W is defined above, R₁ and R₂ are as defined below and n is as defined in claim 1;
R₁ is selected from the group consisting of hydrogen, alkyl, haloalkyl, alkylsulfenyl, alkylsulfmyl, alkylsulfonyl, haloalkylsulfenyl, haloalkylsulfinyl, and haloalkylsulfonyl; and
R₂ is selected from the group consisting of halogen, alkyl and cyano.

13. The compound according to claim 1 which is:
2-chloro-3-cyano-4-thiocyanato-5-methylpyrrole;
4-(2-chloro-3-cyano-5-methylpyrrole)disulfide;
2-chloro-3-cyano-4-(dichlorofluoromethyl)sulfenyl-5-methylpyrrole;
2-methoxy-3-cyano-4-(dichlorofluoromethyl)sulfenyl-5-methylpyrrole;
2-chloro-3-cyano-5-methyl-4-thiouroniumpyrrole hydrobromide;
2-chloro-3-cyano-4-(dichlorofluoromethyl)sulfonyl-5-methylpyrrole;
2-chloro-3-cyano-4-thiocyanato-5-cyclopropylpyrrole;
4-(2-chloro-3-cyano-5-cyclopropylpyrrole)disulfide;
2-chloro-3-cyano-4-(dichlorofluoromethylsulfenyl)-5-cyclopropylpyrrole;
2-chloro-3-cyano-4-thiocyanato-5-isopropylpyrrole;
4-(2-chloro-3-cyano-5-isopropylpyrrole)disulfide;
2-chloro-3-cyano-4-(dichlorofluoromethylsulfenyl)-5-isopropylpyrrole; or
2-chloro-3-cyano-4-(bromodifluoromelhylsulfenyl)-5-methylpyrrole.

14. A compound of the formula:

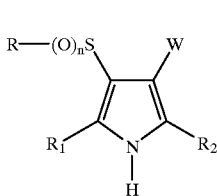

(I)

wherein:
W is cyano, —CO₂H, —CO₂R₃, —CONH₂, —CONHR₃, —CON(R₃)₂, —CSNH₂, —CSNHR₃, —CSN(R₃)₂, —COSH, —COSR₃, —CHO, —CH=NOH, —CH=NOR₃, or nitro;

R is alkyl, cyano, —C(NH$_2$)(=NH) or an acid addition salt thereof, hydrogen, or

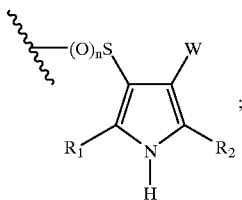

R$_1$ and R$_2$ independently represent hydrogen, halogen, alkyl, haloalkyl, alkoxy, haloalkoxy, alkylsulfenyl, alkylsulfmyl, alkylsulfonyl, haloalkylsulfenyl, haloalkylsulfmyl, haloalkylsulfonyl, cyano, nitro, NR$_{11}$R$_{12}$, formyl, alkylcarbonyl, haloalkylcarbonyl, hydroxyalkylcarbonyl, —CO$_2$H, —CO$_2$R$_3$, aylthiocarbonyl, —CONH$_2$, —CONHR$_3$, —CON(R$_3$)$_2$, bis(alkoxy)methyl, bis(alkylthio)methyl, (alkoxy)(cyano)methyl, (acyloxy)(cyano)methyl, (phenoxy)(cyano)methyl, (alkoxy)(alkylthio)methyl, (alkylamino)(alkoxy)methyl, (alkoxy)(dialkylamino)methyl, (alkylamino)(alkylamino)methyl, (dialkylamino)(dialkylamino)methyl, (alkoxy)(alkoxycarbonyl)methyl, (alkoxy)(aminocarbonyl)methyl, (alkoxy)(alkylaminocarbonyl)methyl, (alkoxy)(dialkylaminocarbonyl)methyl, alkoxyalkyl, hydroxyalkyl, (haloalkoxy)alkyl, (alkoxy)(haloalkyl)alkyl, cyanoalkyl, halogenated cyanoalkyl, alkoxycarbonylalkyl, aminocarbonylalkyl, monoaLkylaminocarbonylalkyl, fonnylalkyl, dialkylaminocarbonylalkyl, alkoxyalkylcarbonyl, alkylsulfenylalkylcarbonyl, alkylsulfmylalkylcarbonyl, alkylsulfonylalkylcarbonyl, cyanoalkylcarbonyl, alkoxycarbonylalkylcarbonyl, aminocarbonylalkylcarbonyl, monalkylaminocarbonylalkylcarbonyl, dialkylaminocarbonylalkylcarbonyl, —CH=N—O—R$_{11}$, amino(thio)carbonyl, monoalkylamino(thio)carbonyl, dialkylamino(thio)carbonyl, or a radical of the formula

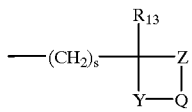

wherein:
R$_{13}$ is hydrogen, alkyl, or haloalkyl;
Y and Z are O, S, SO, SO$_2$, NH, N-alkyl, or N-acyl;

Q is ethylene or propylene optionally substituted with alkyl, haloalkyl, alkoxy, alkoxyalkyl, cyano, hydroxyalkyl, amino, alkylamino, dialkylamino, alkylsulfenyl, alkylsulfmyl, alkylsulfonyl, OH, or SH;

s is 0 to 3;

R$_3$ is alkyl, haloalkyl, hydroxyalkyl or alkoxyalkyl;

R$_{11}$ and R$_{12}$ independently represent H, alkyl, haloalkyl, formyl, alkylcarbonyl, haloalkylcarbonyl, alkoxycarbonyl, haloalkoxycarbonyl, aminocarbonyl, monoalkylaminocarbonyl, dialkylaminocarbonyl, alkylsulfonyl, haloalkylsulfonyl, alkylsulfmyl, haloalkylsulfinyl, allyl, propargyl, halogen, alkoxyalkyl, alkylthioalkyl, alkylsulfmylalkyl, alkylsulfonylalkyl, haloalkoxyalkyl, haloalkylthioalkyl, haloalkylsulfmylalkyl, haloallylsulfonylalkyl, aminoalkyl, monoalkylaminoalkyl, dialkylamninoalkyl, or alkoxycarbonyl; and n is 0, 1 or 2, provided that when R$_1$ is methyl, then R$_2$ is not hydrogen or alkyl, W is not —CO$_2$R$_3$ and n is not 0; and provided that when W is —CO$_2$C$_2$H$_5$, then R is not —C(NH$_2$)(=NH) or an acid addition salt thereof.

15. A compound according to claim 14, in which R is selected from the group consisting of alkyl, cyano, —C(NH$_2$)(=NH) or an acid addition salt thereof, and

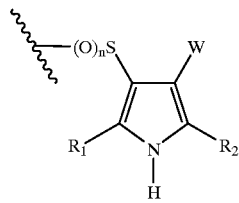

wherein W, R$_1$, R$_2$ and n are as defined in claim 14.

16. The compound according to claim 14 which is:

2-chloro-3-cyano-4-thiocyanato-5-methylpyrrole;

4-(2-chloro-3-cyano-5-methylpyrrole)disulfide;

2-chloro-3-cyano-5-methyl-4-thiouroniumpyrrole hydrobromide;

2-chloro-3-cyano-4-thiocyanato-5-cyclopropylpyrrole;

4-(2-chloro-3-cyano-5-cyclopropylpyrrole)disulfide;

2-chloro-3-cyano-4-thiocyanato-5-isopropylpyrrole; or 4-(2-chloro-3-cyano-5-isopropylpyrrole)disulfide.

* * * * *